United States Patent [19]

Förster et al.

[11] Patent Number: 5,470,841
[45] Date of Patent: * Nov. 28, 1995

[54] METABOLIZABLE PLASMA SUBSTITUTE

[75] Inventors: Harald Förster; Fatima Asskali, both of Frankfurt am Main, Germany; Ernst Nitsch, Linz, Austria

[73] Assignee: Laevosan-Gesellschaft mbH, Linz/Donau, Australia

[ * ] Notice: The portion of the term of this patent subsequent to Jul. 25, 2012, has been disclaimed.

[21] Appl. No.: 178,543

[22] Filed: Jan. 7, 1994

[63] Continuation of PCT/EP92/01552, filed July 9, 1992.

[51] Int. Cl.$^6$ .......................... A61K 31/72; C08B 31/04; C08B 35/02; C08L 3/16

[52] U.S. Cl. .......................... 514/60; 514/832; 514/833; 536/107; 536/110; 536/124

[58] Field of Search .................... 536/107, 110, 536/124; 514/60, 832, 833

[56] References Cited

U.S. PATENT DOCUMENTS

| | | | |
|---|---|---|---|
| 2,362,282 | 11/1944 | Lindsay | 536/110 |
| 3,639,389 | 2/1972 | Hull | 536/110 |
| 3,793,065 | 2/1974 | Morrison et al. | 106/212 |
| 3,937,821 | 2/1976 | Irikura et al. | 514/832 |
| 3,962,465 | 6/1976 | Richter et al. | 426/578 |
| 3,998,753 | 12/1976 | Antoshkiu et al. | 252/363.5 |
| 4,061,610 | 12/1977 | Glowaky et al. | 536/110 |
| 4,211,865 | 7/1980 | Ferruti et al. | 536/49 |
| 4,609,640 | 9/1986 | Morishita et al. | 530/300 |
| 4,615,739 | 10/1986 | Clark et al. | 106/34 |
| 4,629,698 | 12/1986 | Nitsch et al. | 424/101 |
| 4,879,283 | 11/1989 | Belzer et al. | 514/60 |
| 5,006,140 | 4/1991 | Loercks et al. | 524/734 |
| 5,039,520 | 8/1991 | Hunter | 424/83 |
| 5,122,539 | 6/1992 | Abraham et al. | 514/563 |
| 5,200,398 | 4/1993 | Strasberg et al. | 514/23 |

FOREIGN PATENT DOCUMENTS 1476057  6/1977  United Kingdom .

*Primary Examiner*—Ronald W. Griffin
*Attorney, Agent, or Firm*—Nikaido, Marmelstein, Murray & Oram LLP

[57] ABSTRACT

A metabolizable blood plasma substitute is described which contains a starch ester with a molecular weight (Mw) of> 20000 Daltons and a molar substitution of 0.1 to 1.5 as a colloidal component. The starch ester is for example acetyl starch with a molecular weight (Mw) of 200000 to 230000 Daltons and a molar substitution of 0.3 to 0.5.

14 Claims, 3 Drawing Sheets

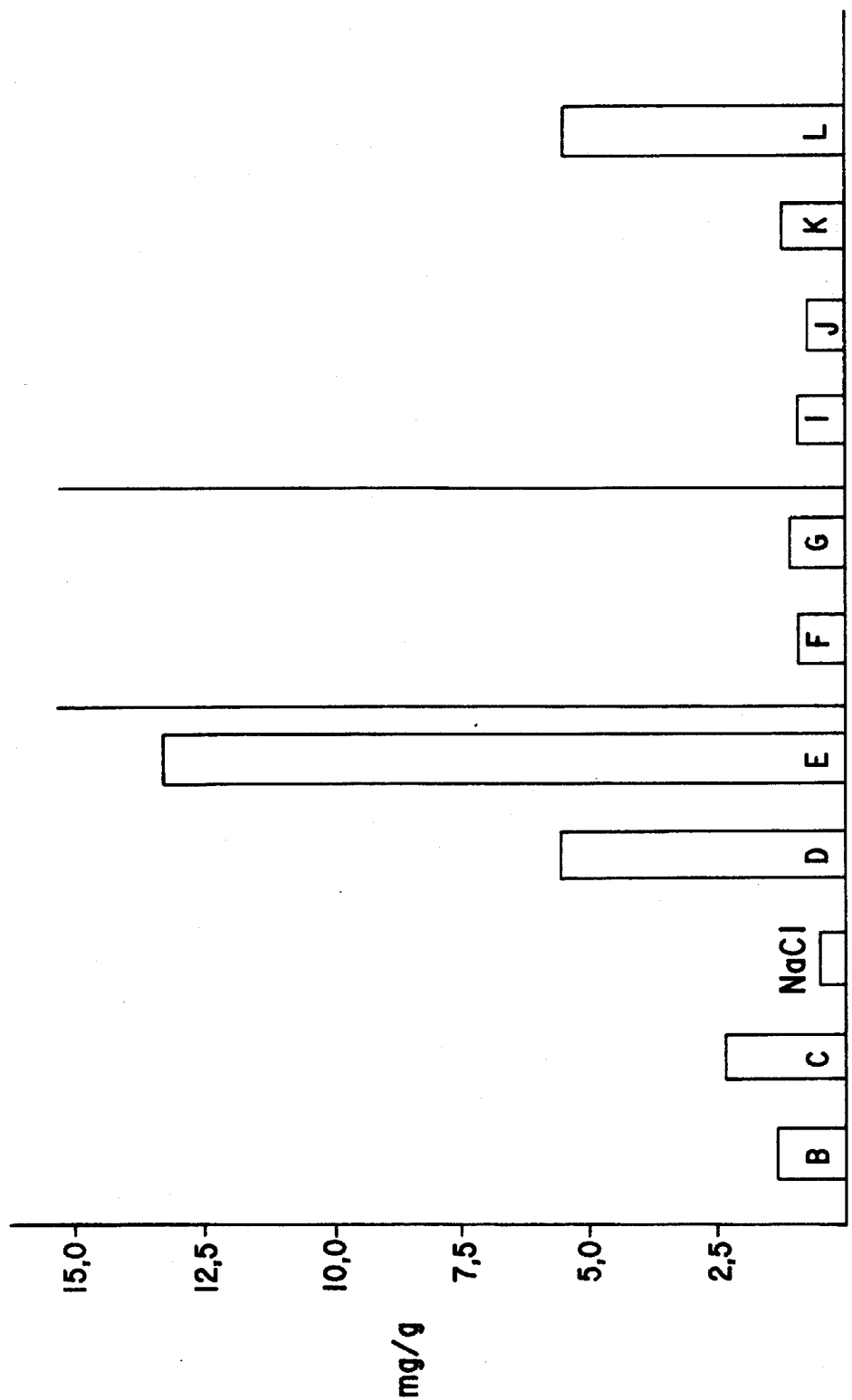

METABOLIZABLE PLASMA SUBSTITUTE

CROSS REFERENCED TO RELATED APPLICATIONS

This application is a continuation-in-part of PCT International Application No. PCT/EP92/01552, filed Jul. 9, 1992, and designating the U.S.

The invention concerns plasma substitute solutions which contain a starch ester as the colloidal component.

For numerous indications e.g. large loss of blood, it is necessary to use colloid-osmotically active substances as plasma substitutes (plasma expanders). These substances serve to maintain the colloid osmotic pressure within the intravascular space as well as to dilute the blood (haemodilution), e.g. in the treatment of circulatory disturbances. There is a steadily increasing need for such plasma substitutes and haemodilution agents.

It is known that polyvinylpyrrolidone, gelatin derivatives, dextran and hydroxyethyl starch can be used for such blood plasma substitutes (cf. e.g. US-A 3,937,821; DE-A 33 13 600; Römpp "Chemielexikon", 9th Vol, page 919, 1509).

At present the polysaccharides dextran and hydroxyethyl starch are mainly used for clinical application. The primary disadvantage of dextran is that anaphylactic reactions can occur due to the presence of preformed antibodies, which make the use of this substance dangerous or complicate it by a compulsory pretreatment with a neutralizing low molecular hapten. Although direct side-effects were only seldom observed in a short-term direct administration of hydroxyethyl starch, the prolonged administration of hydroxyethyl starch is, however, very limited by its storage especially in reticuloendothelial tissue. Hydroxyethyl starch can only be slowly and incompletely degraded by endogenous enzymes because the etherification impedes attack by endogenous glycosidases. Although it is not yet known with certainty whether this storage impairs the function of the reticuloendothelial system, the occurrence of itching for example as a side-effect which is observed when administering hydroxyethyl starch has been linked to this storage.

The object of the present invention is therefore to provide plasma substitutes which avoid the aforementioned disadvantages of the plasma substitutes which up to now have been commonly used and which are not expected to cause any significant side-effects when they are used. In particular the basis for the plasma substitutes should be a substance against which no preformed antibodies are present and which is not stored to a great extent in the organism. This object is achieved by the present invention.

Therefore according to claim 1 the invention concerns a blood plasma substitute containing a starch ester in which the starch is substituted with acyl groups of monocarboxylic acids or dicarboxylic acids or mixtures of mono- and dicarboxylic acids each with 2 to 6 C atoms, with a molecular weight (Mw) of > 20000 Daltons and a molar substitution of 0.1 to 1.5.

Practical embodiments thereof are the subject matter of claims 2 to 8.

It was found that starch esters with organic acids such as e.g. acetyl starch, are very well suited for use in plasma substitutes. Starch esters are cleaved by esterases. The starch which forms in this process is so closely related to engogenous glycogen that the formation of antibodies can be ruled out. It is cleaved into lower molecular fragments (oligosaccharides, isomaltose, maltose) by glycosidases in the same way as endogenous glycogen and can be degraded to form glucose. The organic acids (such as e.g. acetic acid) which form when starch esters are degraded are either metabolized or excreted via the kidney. The glucose which forms during the degradation of starch is subject to physiological metabolism.

The starch esters used according to the invention as a colloidal component of plasma substitute solutions are thus hydrocolloids which are very similar to a physiological (endogenous) substance and which can be almost completely metabolized by enzymatic degradation. Results available up to now show that they do not lead to antibody formation and rule out a storage of the acid esters used according to the invention in the various organs on a large scale or over longer time periods.

An examination of the organs of animals treated with acetyl starch showed that deposition of a small amount of acetyl starch was only found immediately after administration of acetyl starch and 3 hours after the administration, in particular in the kidneys and the lungs. These organs have a strong blood circulation and therefore it cannot be excluded that the acetyl starch present in the blood is also determined in the analysis. However, it was determined that the spleen in particular as a representative of the reticuloendothelial system hardly showed any deposition of acetyl starch. In particular stored acetyl starch was no longer detectable several days after administration of acetyl starch in a single dose of 2 to 8 g/kg in rats. This represents a major advantage compared to hydrocolloids (e.g. dextran or hydroxyethyl starch) used commonly up to now in plasma substitutes; deposits of dextran or of hydroxyethyl starch were still detected in the liver, spleen, lungs and kidneys even weeks and months after administration of dextran or hydroxyethyl starch in comparable amounts in rats under the same conditions.

With regard to their efficacy as plasma substitutes (plasma expanders), the starch esters according to the invention are comparable to the polysaccharides, and in particular hydroxyethyl starch and dextran, which have previously been commonly used for such agents, but compared with these they have the aforementioned advantages. They are therefore excellently suited as a colloidal component of plasma substitute solutions (plasma expanders).

The present invention therefore also concerns the use of the starch esters according to the invention to maintain the colloid osmotic pressure within human or animal intravascular spaces and for blood dilution (haemodilution).

The starch esters used according to the invention are starch esters with a molar substitution MS of 0.1 to 1.5. Starch esters are esters with organic carboxylic acids and in particular with aliphatic mono- and dicarboxylic acids with 2 to 6 carbon atoms such as e.g. acetic acid, propionic acid, butyric acid, isobutyric acid, succinic acid and maleic acid. The molar substitution MS is preferably 0.3 to 0.5. A particularly preferred starch ester according to the invention is acetyl starch, in particular one with a molecular weight (Mw) of 100000 to 200000 Daltons and a molar substitution MS of 0.2 to 0.5.

The starch esters are derived for example from wax-like milo(sorghum) starch, wax-like corn starch or wax-like rice starch. Fractions with an appropriate molecular weight obtained from native products by partial hydrolysis are primarily used and in particular starch esters obtained by partial hydrolytic degradation of starch that is rich in amylopectin and subsequent partial esterification.

The most suitable molar substitution is also especially dependent on the type of starch esters used (type of parent starch, molecular weight and/or ester group). It also influences the retention time in the plasma and thus the duration of action of the starch ester used which can thus be controlled by modification of the degree of substitution.

The starch esters used according to the invention have a lower limit of average molecular weight (Mw) of ca. 20000 Daltons. This lower limit is a consequence of the fact that the molecular weight of the starch esters should be above the renal threshold.

Starch esters with an average molecular weight (Mw) of 40000 to 1000000 Daltons and preferably of 100000 to 450000 Daltons are preferably used.

For application as plasma substitutes or for haemodilution it is necessary to add osmotically active substances apart from the starch ester as the colloidal component. The plasma substitute according to the invention therefore contains the starch ester in combination with a physiologically acceptable osmotically active electrolye and/or other osmotically active substances in aqueous solution. The concentration of the starch ester is preferably 1 to 12 % w/v, in particular 3 to 10 % w/v, in relation to the total plasma substitute.

Electrolytes and their mixtures which come into consideration as the physiologically acceptable electrolytes are those which are usually used in such plasma substitutes i.e. in particular e.g. sodium chloride, calcium chloride, salts of the lower carboxylic acids with 2 to 4 carbon atoms, in particular acetic acid.

The other osmotically active substance can be a lower molecular organic compound and preferably consists of polyvalent alcohols, monosaccharides, disaccharides such as e.g. glycerol, sorbitol, maltose and primarily glucose and/or amino acids.

Those substances which result in an osmolarity of 200 to 450 mosmol/kg and in particular of 250 to 350 mosmol/kg are usually used as osmotically active electrolytes and other osmotically active substances.

The plasma substitutes according to the invention can contain one or several starch esters according to the invention in combination with one or several of the osmotically active substances (electrolyte and/or other osmotically active substances) in water.

The starch esters used according to the invention can be produced according to the application entitled "Process for the production of starch esters for clinical, in particular parenteral use" of the same applicant, file number P 41 23 000.0. The production of the plasma substitutes is carried out in a well-known manner, e.g. by mixing the components in water or an aqueous electrolyte solution, and the starch esters are preferably used in the form of powders obtained by drying, e.g. by spray drying, rotary drying or vacuum drying, and grinding.

It is intended to elucidate the invention in more detail by the following examples.

EXAMPLE 1

Production of plasma substitute solutions

Acetyl starch with an average molecular weight (Mw) of ca. 200000 Daltons and a degree of substitution of 0.3 or 0.5 was used as the starch ester.

The following plasma substitute solutions were prepared from this:

1. Acetyl starch solution at a concentration of 3, 6 and 10 % by weight in physiological saline solution (0.9 % by weight).

2. Acetyl starch solution at a concentration of 6% by weight in 2.5 % by weight glycerol solution (electrolyte-free plasma substitute solution)

EXAMPLE 2

Investigations on biodegradability

The acetyl starch solutions prepared according to example 1 with a concentration of 3, 6 and 10 % by weight acetyl starch (degree of substitution 0.3 or 0.5) in physiological saline solution were administered intravenously into rats (18 ml in 3 hours).

The infusions were very well tolerated and no direct side-effects were detected. Immediately after completion of the infusions dose-dependent blood levels of acetyl starch were present (6 to 25 mg/ml). These blood levels were comparable to those which were obtained using hydroxyethyl starch solutions (HES 200/0.5; Mw ca. 200000 Daltons, molar substitution 0.5 mol). Even 3 hours after completion of the infusion acetyl starch was still detectable in the blood of the animals (1.0 to 10 mg/ml); these amounts also corresponded to the amounts which were obtained under comparable conditions with the hydroxyethyl starch solution (HES 200/0.5). However, 24 hours after completion of the infusion no acetyl starch could be detected in the blood of the treated animals.

FIG. 3 shows the results corresponding to FIG. 2 for the lung.

Figure 1:
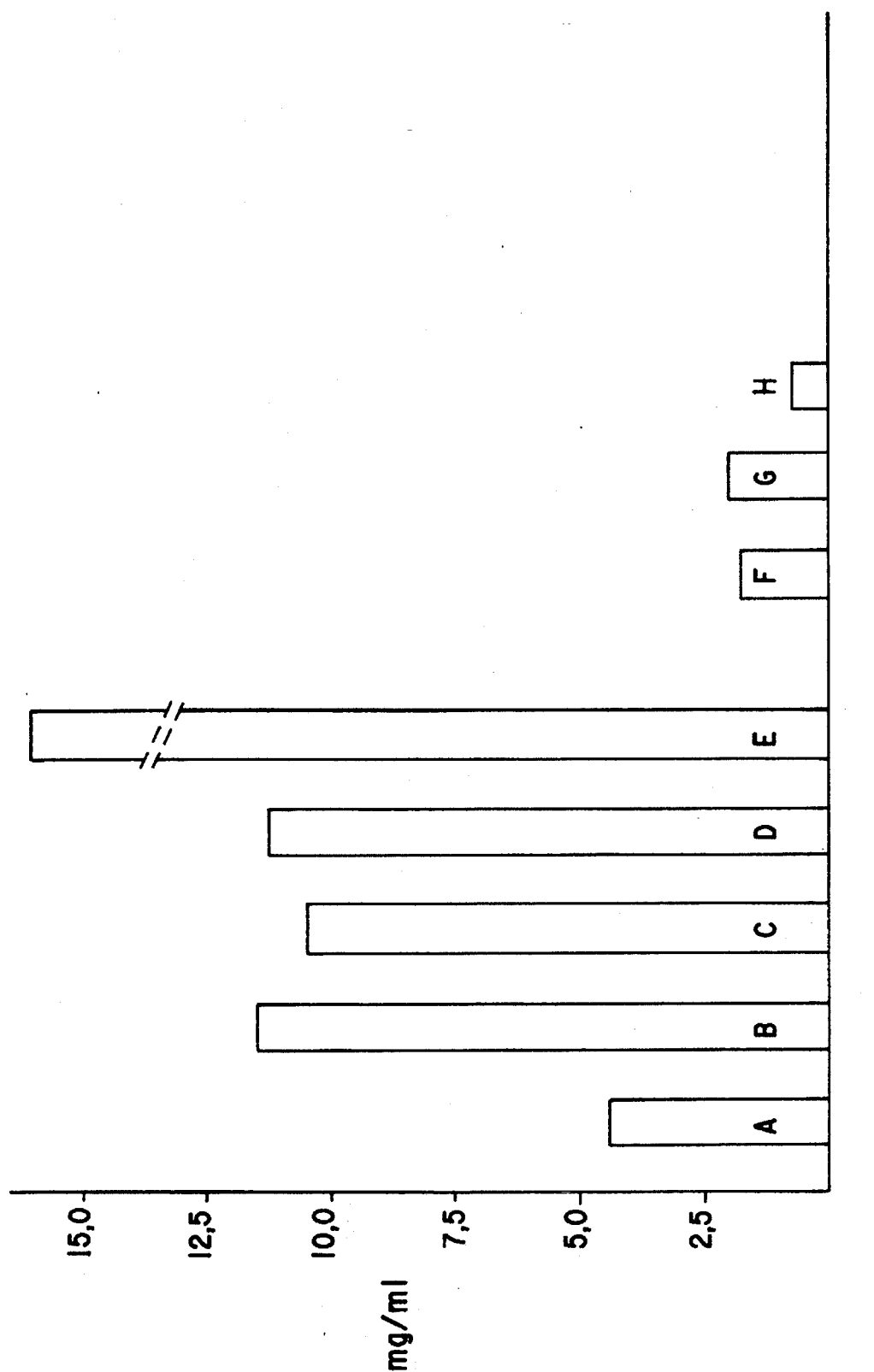
FIG. 1 shows the serum content (in mg/ml) after a three hour infusion which was determined immediately after the infusion was completed (A to E) and 3 hours after completion of the infusion (F, G, H).
Figure 2:
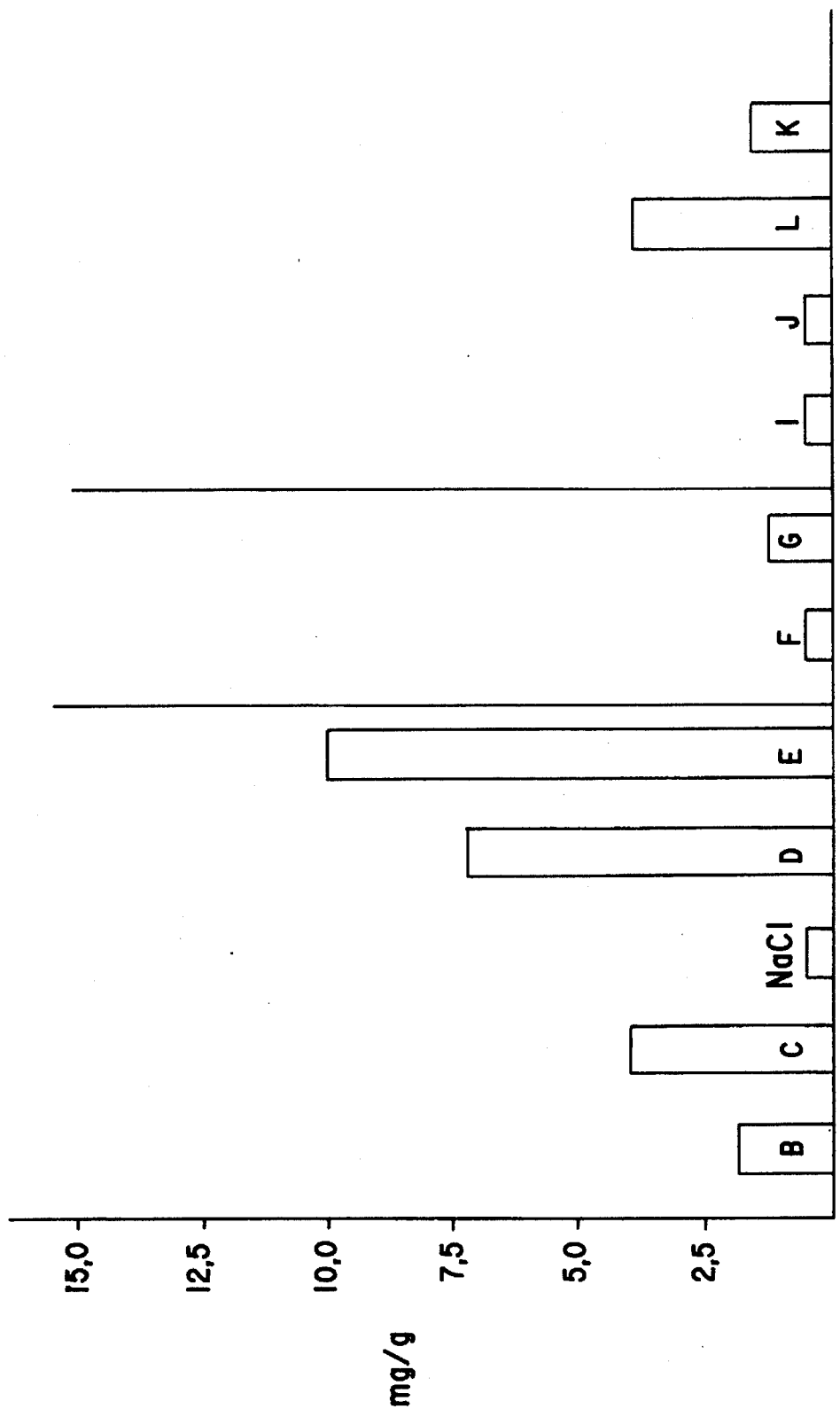
FIG. 2 shows the content of hydrocolloid in the kidney (in mg/g) which was determined immediately after the infusion was completed (B, C, D, E and NaCl), 3 hours after completion of the infusion (F, G) and 18 to 24 hours after completion of the infusion (I, J, K, L).

The data A to L in FIGS. 1 to 3 refer to the following plasma substitute solutions:

A - 3% acetyl starch; B - 6% acetyl starch; C - 10% acetyl starch; D - 6% HES 200/0.5; E - 10% HES 200/0.5; F - 6% acetyl starch; G - 10% acetyl starch; H - 3% acetyl starch; I - 6% acetyl starch; J - 10% acetyl starch; K - 6 % HES 200/0.5; L - 10% HES 200/0.5. NaCl = sodium chloride.

I claim:

1. A blood plasma substitute, comprising a starch ester in aqueous solution, wherein said starch ester is substituted with acyl groups of monocarboxylic acids with 2 to 6 C atoms, dicarboxylic acids with 2 to 6 C atoms or mixtures of said mono and dicarboxylic acids, and wherein said starch ester has a molecular weight (Mw) of > 20000 Daltons and a molar substitution of 0.1 to 1.5.

2. The blood plasma substitute according to claim 1, wherein the molar substitution is 0.2 to 0.7.

3. The blood plasma substitute according to claim 2, wherein the molar substitution is 0.3 to 0.5.

4. The blood plasma substitute according to claim 1, wherein the molecular weight (Mw) of said starch ester is 40,000 to 1,000,000 Daltons.

5. The blood plasma substitute according to claim 4, wherein the molecular weight (Mw) of said starch ester is 100,000 to 450,000 Daltons.

6. The blood plasma substitute according to claim 1, wherein said starch ester is acetyl starch.

7. The blood plasma substitute according to claim 6, wherein said acetyl starch has a molecular weight (Mw) of 100,000 to 200,000 Daltons and a molar substitution of 0.3 to 0.5.

8. A blood plasma substitute, comprising 1 to 12% by weight of a starch ester in combination with a physiologically acceptable osmotically active electrolyte, wherein said starch ester is substituted with acyl groups of monocarboxylic acids with 2 to 6 C atoms, dicarboxylic acids with 2 to 6 C atoms, or mixtures of said mono- and dicarboxylic acids, and wherein said starch ester has a molecular weight (Mw) of > 20000 Daltons and a molar substitution of 0.1 to 1.5.

9. The blood plasma substitute according to claim 8, comprising 3 to 10 % by weight of said starch ester.

10. The blood plasma substitute according to claim 8, further comprising one or more other osmotically active substances in aqueous solution.

11. The blood plasma substitute according to claim 10, wherein the other osmotically active substances are selected from the group consisting of polyvalent alcohols, monosaccharides, disaccharides and amino acids.

12. The blood plasma substitute according to claim 11, wherein the other osmotically active substances are selected from the group consisting of glycerol and glucose.

13. A method for maintaining the colloid osmotic pressure within human or animal intravascular spaces, comprising administering to a patient an amount of a blood plasma substitute effective to maintain the colloid osmotic pressure within human or animal intravascular spaces, wherein said blood plasma substitute comprises a starch ester which is substituted with acyl groups of monocarboxylic acids with 2 to 6 C atoms, dicarboxylic acids with 2 to 6 C atoms or mixtures of said mono- and dicarboxylic acids, and wherein said starch ester has a molecular weight (Mw) of > 20000 Daltons and a molar substitution of 0.1 to 1.5.

14. A method for diluting blood (hemodilution), comprising adding to a volume of blood, an amount of a blood plasma substitute effective to dilute said blood, wherein said blood plasma substitute comprises a starch ester which is substituted with acyl groups of monocarboxylic acids with 2 to 6 C atoms, dicarboxylic acids with 2 to 6 C atoms or mixtures of said mono- and dicarboxylic acids, and wherein said starch ester has a molecular weight (Mw) of > 20000 Daltons and a molar substitution of 0.1 to 1.5.

* * * * *